(12) United States Patent
Matusz et al.

(10) Patent No.: US 7,932,407 B2
(45) Date of Patent: Apr. 26, 2011

(54) OLEFIN EPOXIDATION PROCESS AND A CATALYST FOR USE IN THE PROCESS

(75) Inventors: Marek Matusz, Houston, TX (US); Ruth Mary Kowaleski, Cypress, TX (US)

(73) Assignee: Shell Oil Company, Houston, TX (US)

( * ) Notice: Subject to any disclaimer, the term of this patent is extended or adjusted under 35 U.S.C. 154(b) by 493 days.

(21) Appl. No.: 10/816,080

(22) Filed: Apr. 1, 2004

(65) Prior Publication Data
US 2004/0198993 A1 Oct. 7, 2004

Related U.S. Application Data

(60) Provisional application No. 60/459,502, filed on Apr. 1, 2003.

(51) Int. Cl.
*C07D 301/10* (2006.01)
*C07D 301/03* (2006.01)

(52) U.S. Cl. .................. 549/536; 549/534

(58) Field of Classification Search .................. 549/536, 549/534
See application file for complete search history.

(56) References Cited

U.S. PATENT DOCUMENTS

| | | | |
|---|---|---|---|
| 2,279,470 A | 4/1942 | Law et al. | 260/348 |
| 3,962,285 A | 6/1976 | Cusumano | 260/348.5 R |
| 4,055,579 A | 10/1977 | Cocuzza et al. | 260/348.34 |
| 4,761,394 A | 8/1988 | Lauritzen | 502/348 |
| 4,766,105 A | 8/1988 | Lauritzen | 502/216 |
| 4,808,738 A | 2/1989 | Lauritzen | 549/536 |
| 4,810,689 A | 3/1989 | Hayden | 502/347 |
| 4,820,675 A | 4/1989 | Lauritzen | 502/216 |
| 4,822,900 A | 4/1989 | Hayden | 549/534 |
| 4,829,044 A | 5/1989 | Boxhoorn et al. | 502/348 |
| 4,831,162 A | 5/1989 | Nakajima et al. | 549/534 |
| 4,833,261 A | 5/1989 | Lauritzen | 549/536 |
| 4,845,296 A | 7/1989 | Ahmed et al. | 564/477 |
| 4,874,739 A | 10/1989 | Boxhoorn | 502/218 |
| 4,874,879 A | 10/1989 | Lauritzen et al. | 549/536 |
| 4,908,343 A | 3/1990 | Bhasin | 502/218 |
| 4,950,773 A | 8/1990 | Monnier et al. | 549/534 |
| 5,011,807 A | 4/1991 | Hayden et al. | 502/218 |
| 5,100,859 A | 3/1992 | Gerdes et al. | 502/439 |
| 5,102,848 A | 4/1992 | Soo et al. | 502/218 |
| 5,145,824 A | 9/1992 | Buffum et al. | 502/216 |
| 5,155,242 A | 10/1992 | Shankar et al. | 549/534 |
| 5,187,140 A | 2/1993 | Thorsteinson et al. | 502/348 |
| 5,262,551 A | 11/1993 | Horrell, Jr. et al. | 549/534 |
| 5,364,826 A | 11/1994 | Kemp | 502/315 |
| 5,380,697 A | 1/1995 | Matusz et al. | 502/348 |
| 5,380,885 A | 1/1995 | Kemp | 549/536 |
| 5,387,751 A | 2/1995 | Hayden et al. | 549/534 |
| 5,418,202 A | 5/1995 | Evans et al. | 502/348 |
| 5,447,897 A | 9/1995 | Kemp | 502/303 |
| 5,486,628 A | 1/1996 | Kemp | 549/536 |
| 5,504,052 A | 4/1996 | Rizkalla et al. | 502/347 |
| 5,504,053 A | 4/1996 | Chou et al. | 502/348 |
| 5,545,603 A | 8/1996 | Kemp | 502/347 |
| 5,597,773 A | 1/1997 | Evans et al. | 549/534 |
| 5,663,385 A | 9/1997 | Kemp | 549/536 |
| 5,703,253 A | 12/1997 | Evans et al. | 549/536 |
| 5,739,075 A | 4/1998 | Matusz | 502/302 |
| 5,801,259 A | 9/1998 | Kowaleski | 549/536 |
| 5,864,047 A | 1/1999 | Gaffney | 549/536 |
| 6,011,163 A | 1/2000 | Barnicki et al. | 549/534 |
| 6,368,998 B1 | 4/2002 | Lockemeyer | 502/347 |
| 6,372,925 B1 | 4/2002 | Evans et al. | 549/536 |
| 6,717,001 B2 | 4/2004 | Evans et al. | 549/536 |
| 7,193,094 B2 | 3/2007 | Chipman et al. | 549/536 |

FOREIGN PATENT DOCUMENTS

| | | | |
|---|---|---|---|
| AU | 18818/70 | 2/1927 | |
| BE | A707567 | 5/1968 | |
| CA | 488990 | 12/1952 | 260/372.7 |
| CA | 1286687 | 7/1991 | |
| EP | 0057066 | 8/1982 | |
| EP | 003642 | 7/1984 | |
| EP | 266015 A1 | 5/1988 | |
| EP | 0266852 | 5/1988 | |
| EP | 0299569 | 1/1989 | |
| EP | 0352849 | 1/1990 | |
| EP | 352850 | 1/1990 | |
| EP | 0357292 | 3/1990 | |
| EP | 0425020 | 5/1991 | |
| EP | 0480537 | 11/1991 | |
| EP | 0480538 | 4/1992 | |
| EP | 0496470 | 7/1992 | 301/10 |
| EP | 0567273 | 10/1993 | |
| EP | 0393785 | 1/1995 | |
| EP | 1458698 | 9/2004 | |
| EP | 1458699 | 9/2004 | |
| GB | 1055147 | 1/1967 | |
| GB | 1213483 | 11/1970 | |

(Continued)

OTHER PUBLICATIONS

Kirk-Othmer Ency. of Chem. Tech., $3^{rd}$ Ed., vol. 9 (1980), pp. 445-447.

(Continued)

*Primary Examiner* — Janet L. Andres
*Assistant Examiner* — Raymond Covington

(57) ABSTRACT

A process for the epoxidation of an olefin, which process comprises reacting a feed comprising an olefin, oxygen and an organic halide, in the presence of a catalyst comprising silver and rhenium deposited on a carrier, wherein the catalyst comprises rhenium in a quantity of at most 1.5 mmole/kg, relative to the weight of the catalyst, and at most 0.0015 mmole/$m^2$, relative to the surface area of the carrier, and in which process the reaction temperature is increased to at least partly reduce the effect of loss of activity of the catalyst while the organic halide is present in a relative quantity Q which is maintained constant as defined herein.

12 Claims, No Drawings

FOREIGN PATENT DOCUMENTS

| | | |
|---|---|---|
| GB | 1314613 | 4/1973 |
| JP | 2002248351 | 9/2002 |
| WO | WO9507139 | 3/1995 |
| WO | 95/17957 | 7/1995 |
| WO | WO97/10232 | 3/1997 |
| WO | WO9713579 | 4/1997 |
| WO | WO97/28142 | 8/1997 |
| WO | WO9858920 | 12/1998 |
| WO | WO-00/15333 | 3/2000 |
| WO | WO-00/15334 | 3/2000 |
| WO | WO/00/15335 | 3/2000 |
| WO | WO0196324 | 12/2001 |

OTHER PUBLICATIONS

Written Opinion of the International Searching Authority for PCT/EP99/06725 (WO 2004/089537).

Written Opinion of the International Preliminary Examining Authority, dated Mar. 29, 2005, for PCT/US2004/009883.

International Preliminary Report on Patentability, dated Jul. 1, 2005, for PCT/US2004/009883.

International Search Report, dated Oct. 12, 2004, for PCT/US2004/009883.

Serafin, JG, et al "Surface. Science & the Silver-Catalyzed" Journal of Molecular Catalysis A :Chemical, vol. 131, 1998, pp. 157-168, XP002230219, p. 162.

"Ethylene Oxide Synthesis," by J. M. Berty, Applied Industrial Catalysis, vol. 1, 1983, pp. 207-239.

"Chlorierte Kohlenwasserstoffe also Inhibitoren in der Tethylenoxid-Synthese Teil 2: Verbrauchsreaktionen von chemisorbiertem Chlor," by Thomas Reib and Gerhard Luft, Chem.-Ing.-Tech. 67 (1995), pp. 589-591. (English translation provided).

Advanced Inorganic Chemistry A Comprehensive Test, F. Albert Cotton and Geoffrey Wilkenson, F.R.S., Interscience Pu. A Division of John Wiley & Sons, New York, London, Sydney (1966), p. 335.

Brunauer, S., Emett, P.Y. and Teller, E., J. Am. Chem. Soc., 60, 309-316 (1938).

Reiss, Luft, Chenue Ingenieur Technik (1997), 69(ii), 1638-1641. (English translation provided).

OLEFIN EPOXIDATION PROCESS AND A CATALYST FOR USE IN THE PROCESS

This application claims the benefit of U.S. Provisional Application No. 60/459,502 filed Apr. 1, 2003, the entire disclosure of which is hereby incorporated by reference.

FIELD OF THE INVENTION

The present invention relates to a process for the production of an olefin oxide, a 1,2-diol, a 1,2-diol ether or an alkanolamine and to a catalyst for use in the said process.

BACKGROUND OF THE INVENTION

In olefin epoxidation an olefin is reacted with oxygen to form an olefin epoxide, using a catalyst comprising a silver component, usually with one or more further elements deposited therewith on a carrier. The olefin oxide may be reacted with water, an alcohol or an amine to form a 1,2-diol, a 1,2-diol ether or an alkanolamine. Thus, 1,2-diols, 1,2-diol ethers and alkanolamines may be produced in a multi-step process comprising olefin epoxidation and converting the formed olefin oxide with water, an alcohol or an amine.

The performance of the silver containing catalyst may be assessed on the basis of selectivity, activity and stability of operation in the olefin epoxidation. The selectivity is the molar fraction of the converted olefin yielding the desired olefin oxide. As the catalyst ages, the fraction of the olefin reacted normally decreases with time and to maintain a constant level of olefin oxide production the temperature of the reaction is increased. However this adversely affects the selectivity of the conversion to the desired olefin oxide. In addition, the equipment used can tolerate temperatures only up to a certain level so that it is necessary to terminate the reaction when the reaction temperature would reach a level inappropriate for the reactor. Thus the longer the selectivity can be maintained at a high level and the epoxidation can be performed at an acceptably low reaction temperature, the longer the catalyst charge can be kept in the reactor and the more product is obtained. Quite modest improvements in the maintenance of selectivity over long periods yields huge dividends in terms of efficiency in the olefin epoxidation process and, if applicable, also in the overall process for the production of a 1,2-diol, a 1,2-diol ether or an alkanolamine.

An organic halide, for example a chlorohydrocarbon, may be added to the feed to an epoxidation reactor as a reaction modifier for increasing the selectivity. The reaction modifier suppresses the undesirable oxidation of olefin or olefin oxide to carbon dioxide and water, relative to the desired formation of olefin oxide, by a so-far unexplained mechanism.

U.S. Pat. No. 4,766,105 and U.S. Pat. No. 4,761,394 disclose that rhenium may be employed as a further element in the silver containing catalyst with the effect that the initial selectivity of the olefin epoxidation is increased. Working examples given in these US patents show a trend towards a higher selectivity at higher rhenium levels up to about 3 mmole rhenium/kg catalyst, on a carrier having a surface area of 0.42 m$^2$/g.

EP-A-352850 teaches that the then newly developed catalysts, comprising silver supported on alumina, promoted with alkali metal and rhenium have a very high selectivity. It was found that when operating with the newly developed commercial catalysts comprising silver, alkali metal promoters, and a rhenium promoter on an alumina support, longer catalyst lives are obtained when the chlorohydrocarbon level is increased over the period of operation of the catalyst, that is along with the reaction temperature increase as commonly practiced to reduce the effects of catalyst deactivation.

Not withstanding the improvements already achieved, there is a desire to further improve the performance of a rhenium containing catalyst, in particular increase the stability of operation of such catalyst.

SUMMARY OF THE INVENTION

The invention provides a process for the epoxidation of an olefin, which process comprises reacting a feed comprising an olefin, oxygen and an organic halide, in the presence of a catalyst comprising silver and rhenium deposited on a carrier, wherein the catalyst comprises rhenium in a quantity of at most 1.5 mmole/kg, relative to the weight of the catalyst, and at most 0.0015 mmole/m$^2$, relative to the surface area of the carrier, and in which process the reaction temperature is increased to at least partly reduce the effect of loss of activity of the catalyst while the organic halide is present in a relative quantity Q which is maintained constant, which relative quantity Q is the ratio of an effective molar quantity of active halogen species present in the feed to an effective molar quantity of hydrocarbons present in the feed.

The invention also provides a process for the production of a 1,2-diol, a 1,2-diol ether or an alkanolamine comprising converting an olefin oxide into the 1,2-diol, the 1,2-diol ether or the alkanolamine wherein the olefin oxide has been obtained by a process for the epoxidation of an olefin comprising reacting the olefin with oxygen in accordance with this invention.

In preferred embodiments, amongst others, the invention also provides a catalyst comprising silver and rhenium deposited on a carrier, wherein the catalyst comprises rhenium in a quantity of at most 0.9 mmole/kg, relative to the weight of the catalyst, and at most 0.0015 mmole/m$^2$, relative to the surface area of the carrier.

The invention also provides a process for the preparation of a catalyst according to these preferred embodiments of the invention which process comprises depositing silver and a sufficient quantity of rhenium on a carrier.

DETAILED DESCRIPTION OF THE INVENTION

It is particularly advantageous to employ in accordance with the present invention a catalyst comprising a silver component and a rhenium containing component, wherein the rhenium containing component is present in a relatively small quantity, as defined for use in this invention. Even though such catalysts may have a lower initial selectivity than achievable by employing more rhenium, it has been found that during use they retain their selectivity better, even such that after a certain period of use they outperform the catalysts which comprise more rhenium and they have accordingly a longer service life. These technical effects are obtained when during the use of the catalyst, during which the reaction temperature is increased to substantially maintain olefin oxide production, the relative quantity Q is substantially not increased, but kept constant, typically at a relatively low level. This is non-obvious in view of the prior art acknowledged hereinbefore. U.S. Pat. No. 4,766,105 and U.S. Pat. No. 4,761,394 are concerned with the initial performance of the catalysts and their teaching is such that a skilled person would apply a relatively high rhenium level to obtain the maximum benefit of an improved initial selectivity. U.S. Pat. No. 4,766,105 and U.S. Pat. No. 4,761,394 are silent with respect to ageing related phenomena of the catalysts disclosed therein. EP-A-352850 teaches that for an improved catalyst life the organic halide level is increased over the period of operation of the catalyst. At the constant level of hydrocarbons present in the feed, as applied in the Examples of EP-A-352850, an increase of the organic halide level effectively leads to an increase of the relative quantity Q.

The definition of a relative quantity Q, as provided herein before, may be clarified in brief, as follows. More details are provided hereinafter. More of the organic halide will generally be needed to achieve a certain effect as the concentration of hydrocarbons in the feed changes to a higher value, and vice versa. It is thought that, unlike other components of the feed, the hydrocarbons present (for example, the olefin and saturated hydrocarbons, if present) have an ability to remove or strip organic halide from the catalyst and it is the concentration of active halogen species on the catalyst which needs to be maintained, as opposed to the concentration of the organic halide in the reaction mixture at places other than the catalyst surface. For this reason, the relative quantity Q of the organic halide is considered. The relative quantity Q is basically the ratio of the molar quantity of the organic halide to the molar quantity of hydrocarbons as present in the feed. However, as there may be differences in the removing/stripping behavior of the various hydrocarbons in the feed, it may be preferred, when calculating Q, to replace the molar quantity of hydrocarbons by a-so-called-effective molar quantity of hydrocarbons. The effective molar quantity of hydrocarbons in the feed can be calculated from the feed composition (as set out hereinafter), such that it accounts for the differences in the removing/stripping behavior between the hydrocarbons present. There may also be differences in the behavior of different organic halides, while in practice a mixture of organic halides is frequently present. Therefore it may be preferred, when calculating Q, also to replace the molar quantity of the organic halide by a-so-called-effective molar quantity of active species of the organic halide. The effective molar quantity of active species of the organic halide in the feed can be calculated from the feed composition (as set out hereinafter), such that it accounts for the differences in the behavior of different organic halides.

The carrier for use in this invention may be based on a wide range of materials. Such materials may be natural or artificial inorganic materials and they may include refractory materials, silicon carbide, clays, zeolites, charcoal and alkaline earth metal carbonates, for example calcium carbonate. Preferred are refractory materials, such as alumina, magnesia, zirconia and silica. The most preferred material is α-alumina. Typically, the carrier comprises at least 85% w, more typically 90% w, in particular 95% w α-alumina, frequently up to 99.9% w α-alumina, relative to the weight of the carrier. Other components of the α-alumina carrier may comprise, for example, silica, alkali metal, for example sodium and/or potassium, and/or alkaline earth metal, for example calcium and/or magnesium.

The surface area of the carrier may suitably be at least 0.1 $m^2/g$, preferably at least 0.3 $m^2/g$, more preferably at least 0.5 $m^2/g$, and in particular at least 0.6 $m^2/g$, relative to the weight of the carrier; and the surface area may suitably be at most 10 $m^2/g$, preferably at most 5 $m^2/g$, and in particular at most 3 $m^2/g$, relative to the weight of the carrier. "Surface area" as used herein is understood to relate to the surface area as determined by the B.E.T. (Brunauer, Emmett and Teller) method as described in Journal of the American Chemical Society 60 (1938) pp. 309-316. High surface area carriers, in particular when they are α-alumina carriers optionally comprising in addition silica, alkali metal and/or alkaline earth metal, provide improved performance and stability of operation. However, when the surface area is very large, carriers tend to have lower crush strength. Further, it is more difficult to prepare a high surface area α-alumina carrier.

The water absorption of the carrier is typically in the range of from 0.2 to 0.8 g/g, preferably in the range of from 0.3 to 0.7 g/g. A higher water absorption may be in favour in view of a more efficient deposition of silver and further, elements, if any, on the carrier by impregnation. However, at a higher water absorption, the carrier, or the catalyst made therefrom, may have lower crush strength. As used herein, water absorption is deemed to have been measured in accordance with ASTM C393, and water absorption is expressed as the weight of the water that can be absorbed into the pores of the carrier, relative to the weight of the carrier.

It is preferred that the carrier particles are in the form of formed bodies, the size of which is in general determined by the dimensions of a reactor in which they are to be deposited. Generally however it is found very convenient to use particles such as formed bodies in the form of powdery particles, trapezoidal bodies, cylinders, saddles, spheres, doughnuts, and the like. The cylinders may be solid or hollow, straight or bend, and they may have their length and cross-sectional dimensions about the same and from 5 to 10 mm.

The performance of the catalyst may be enhanced if the carrier is washed, to remove soluble residues, before deposition of other catalyst ingredients on the carrier. On the other hand, unwashed carriers may also be used successfully. A useful method for washing the carrier comprises washing the carrier in a continuous fashion with hot, demineralised water, until the electrical conductivity of the effluent water does not further decrease. A suitable temperature of the demineralised water is in the range of 80 to 100° C., for example 90° C. or 95° C. Reference may be made to U.S. Pat. No. 6,368,998, which is incorporated herein by reference.

The preparation of the catalysts is known in the art and the known methods are applicable to the preparation of the catalyst. Methods of preparing the catalyst include impregnating the carrier with a silver compound and performing a reduction to form metallic silver particles. Reference may be made, for example, to U.S. Pat. No. 5,380,697, U.S. Pat. No. 5,739,075, EP-A-266015, U.S. Pat. No. 6,368,998, WO-00/15333, WO-00/15334 and WO-00/15335, which are incorporated herein by reference.

The reduction of cationic silver to metallic silver may be accomplished during a step in which the catalyst is dried, so that the reduction as such does not require a separate process step. This may be the case if the impregnation solution comprises a reducing agent, for example, an oxalate, as described in the Examples hereinafter. Such drying step is suitably carried out at a reaction temperature of at most 300° C., preferably at most 280° C., more preferably at most 260° C., and suitable at a reaction temperature of at least 200° C., preferably at least 210° C., more preferably at least 220° C., suitably for a period of time of at least 1 minute, preferably at least 2 minutes, and suitably for a period of time of at most 20 minutes, preferably at most 15 minutes, more preferably at most 10 minutes.

The catalyst comprises silver as a catalytically active metal. Appreciable catalytic activity is obtained by employing a silver content of the catalyst of at least 10 g/kg, relative to the weight of the catalyst. Preferably, the catalyst comprises silver in a quantity of from 50 to 500 g/kg, more preferably from 100 to 400 g/kg, for example 105 g/kg, or 120 g/kg, or 190 g/kg, or 250 g/kg, or 350 g/kg, relative to the weight of the catalyst.

The catalyst also comprises rhenium, which terminology includes rhenium as such and compounds of rhenium. Rhenium may typically be present in a quantity of at least 0.1 mmole/kg, more typically at least 0.2 mmole/kg, and preferably at least 0.6 mmole/kg, in particular at least 0.7 mmole/kg, relative to the weight of the catalyst. Rhenium is present in a quantity of at most 1.5 mmole/kg, preferably at most 1.2 mmole/kg, more preferably at most 0.9 mmole/kg, in particular at most 0.8 mmole/kg, relative to the weight of the catalyst. In accordance with this invention, rhenium is present in a quantity of at most 0.0015 mmole/m$^2$, relative to the surface area of the carrier. Preferably, the quantity of rhenium is at most 0.0013 mmole/m$^2$, more preferably at most 0.0012 mmole/m$^2$, relative to the surface area of the carrier. Preferably, the quantity of rhenium is at least 0.00001 mmole/m$^2$, more preferably at least 0.00005 mmole/m$^2$, especially 0.0001 mmole/m$^2$, relative to the surface area of the carrier. The form in which rhenium may be deposited onto the carrier is not material to the invention. For example, rhenium may suitably be provided as an oxide or as an oxyanion, for example, as a rhenate or perrhenate, in salt or acid form.

The catalyst preferably comprises silver, rhenium, and a further element or compound thereof. Eligible further elements may be selected from the group of nitrogen, sulfur, phosphorus, boron, fluorine, Group IA metals, Group IIA metals, molybdenum, tungsten, chromium, titanium, hafnium, zirconium, vanadium, thallium, thorium, tantalum, niobium, gallium and germanium and mixtures thereof. Preferably the Group IA metals are selected from lithium, potassium, rubidium and cesium. Most preferably the Group IA metal is lithium, potassium and/or cesium. Preferably the Group IIA metals are selected from calcium and barium. Typically, the further element is present in the catalyst in a quantity of from 0.01 to 500 mmole/kg, more typically from 0.05 to 100 mmole/kg, calculated as the element on the total catalyst. Where possible, the further element may suitably be provided as an oxyanion, for example, as a sulfate, nitrate, nitrite, borate or molybdate, in salt or acid form. Salts of Group IA metals or Group IIA metals are suitable.

Tungsten may typically be present in an amount in the range of from 0.05 to 20 mmole/kg, such as 0.1 mmole/kg, or 0.5 mmole/kg, or 1 mmole/kg, or 1.5 mmoles/kg, or 5 mmole/kg, or 15 mmole/kg; molybdenum may typically be present in an amount in the range of from 1 to 40 mmole/kg, such as 2.3 mmole/kg, or 12 mmole/kg, or 25 mmole/kg; and the alkali metal may each typically be present in amount of from 5 to 100 mmole/kg. Suitable amounts for lithium are for example 5 mmole/kg, or 10 mmole/kg, or 30 mmole/kg, or 40 mmole/kg, or 50 mmole/kg, or 60 mmole/kg. Suitable amounts for cesium are for example 2 mmole/kg, or 3 mmole/kg, or 5 mmole/kg, or 7 mmole/kg, or 10 mmole/kg, or 15 mmole/kg, or 33 mmole/kg, or 47 mmole/kg.

If tungsten and/or molybdenum are present, the molar ratio of the quantity of rhenium to the total quantity of tungsten and molybdenum may typically be in the range of from 0.5 to 5, preferably 0.7 to 3, for example 2.

Of special preference are the catalysts of this invention which comprise silver, rhenium or compound thereof, a Group IA metal or compound thereof, in particular lithium and/or cesium, and optionally a rhenium copromoter selected from tungsten, molybdenum, chromium, sulfur, phosphorus, boron, and compounds thereof. If present, preferred amounts of the rhenium co-promoter are from 0.1 to 30 mmole/kg, based on the total of the relevant elements, viz. tungsten, molybdenum, chromium, sulfur, phosphorus and/or boron, relative to the weight of the catalyst.

As used herein, the quantity of alkali metal present in the catalysts is deemed to be the quantity in so far as it can be extracted from the catalysts with de-ionized water at 100° C. The extraction method involves extracting a 10-gram sample of the catalyst three times by heating it in 20 ml portions of de-ionized water for 5 minutes at 100° C. and determining in the combined extracts the relevant metals by using a known method, for example atomic absorption spectroscopy.

As used herein, the quantity of alkaline earth metal present in the catalysts is deemed to the quantity in so far as it can be extracted from the catalysts with 10% w nitric acid in de-ionized water at 100° C. The extraction method involves extracting a 10-gram sample of the catalyst by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

Although the present epoxidation process may be carried out in many ways, it is preferred to carry it out as a gas phase process, i.e. a process in which the feed is contacted in the gas phase with the catalyst which is present as a solid material, typically in a packed bed. Generally the process is carried out as a continuous process.

The olefin for use in the present epoxidation process may be any olefin, such as an aromatic olefin, for example styrene, or a di-olefin, whether conjugated or not, for example 1,9-decadiene or 1,3-butadiene. Typically, the olefin is a monoolefin, for example 2-butene or isobutene. Preferably, the olefin is a mono-α-olefin, for example 1-butene or propylene. The most preferred olefin is ethylene.

The olefin concentration in the feed may be selected within a wide range. Typically, the olefin concentration in the feed will be at most 80 mole-%, relative to the total feed. Preferably, it will be in the range of from 0.5 to 70 mole-%, in particular from 1 to 60 mole-%, on the same basis. As used herein, the feed is considered to be the composition which is contacted with the catalyst.

The present epoxidation process may be air-based or oxygen-based, see "Kirk-Othmer Encyclopedia of Chemical Technology", 3$^{rd}$ edition, Volume 9, 1980, pp. 445-447. In the air-based process air or air enriched with oxygen is employed as the source of the oxidizing agent while in the oxygen-based processes high-purity (at least 95 mole-%) oxygen is employed as the source of the oxidizing agent. Presently most epoxidation plants are oxygen-based and this is a preferred embodiment of the present invention.

The oxygen concentration in the feed may be selected within a wide range. However, in practice, oxygen is generally applied at a concentration which avoids the flammable regime. Typically, the concentration of oxygen applied will be within the range of from 1 to 15 mole-%, more typically from 2 to 12 mole-% of the total feed.

In order to remain outside the flammable regime, the concentration of oxygen in the feed may be lowered as the concentration of the olefin is increased. The actual safe operating ranges depend, along with the feed composition, also on the reaction conditions such as the reaction temperature and the pressure.

An organic halide is present in the feed as a reaction modifier for increasing the selectivity, suppressing the undesirable oxidation of olefin or olefin oxide to carbon dioxide and water, relative to the desired formation of olefin oxide. Organic halides are in particular organic bromides, and more in particular organic chlorides. Preferred organic halides are chlorohydrocarbons or bromohydrocarbons. More preferably they are selected from the group of methyl chloride, ethyl chloride, ethylene dichloride, ethylene dibromide, vinyl chloride or a mixture thereof. Most preferred are ethyl chloride and ethylene dichloride.

The organic halides are generally effective as reaction modifier when used in low concentration in the feed, for example up to 0.01 mole-%, relative to the total feed. In particular when the olefin is ethylene, it is preferred that the organic halide is present in the feed at a concentration of at most $50 \times 10^{-4}$ mole-%, in particular at most $20 \times 10^{-4}$ mole-%, more in particular at most $15 \times 10^{-4}$ mole-%, relative to the total feed, and preferably at least $0.2 \times 10^{-4}$ mole-%, in particular at least $0.5 \times 10^{-4}$ mole-%, more in particular at least $1 \times 10^{-4}$ mole-%, relative to the total feed.

In addition to the olefin, oxygen and the organic halide, the feed may contain one or more optional components, for example carbon dioxide, inert gases and saturated hydrocarbons. Carbon dioxide is a by-product in the epoxidation process. However, carbon dioxide generally has an adverse effect on the catalyst activity. Typically, a concentration of carbon dioxide in the feed in excess of 25 mole-%, preferably in excess of 10 mole-%, relative to the total feed, is avoided. A concentration of carbon dioxide as low as 1 mole-% or lower, relative to the total feed, may be employed. Inert gases, for example nitrogen or argon, may be present in the feed in a concentration of from 30 to 90 mole-%, typically from 40 to 80 mole-%. Suitable saturated hydrocarbons are methane and ethane. If saturated hydrocarbons are present, they may be present in a quantity of up to 80 mole-%, relative to the total feed, in particular up to 75 mole-%. Frequently they are present in a quantity of at least 30 mole-%, more frequently at least 40 mole-%. Saturated hydrocarbons may be added to the feed in order to increase the oxygen flammability limit.

The relative quantity Q is the ratio of the effective molar quantity of active halogen species present in the feed to the effective molar quantity of hydrocarbons present in the feed, both molar quantities being expressed in the same units, for example as mole-%, based on the total feed.

For the purpose of calculating the effective molar quantity of active halogen species present in the feed and the value of Q, the number of active halogen species present in the feed is deemed to be the number of halogen atoms present. This implies, for example, that 1 mole of ethylene dichloride provides about 2 moles of active species, i.e. all of the chlorine atoms present provide an active species. On the other hand, it has also been found that organic halides which are methyl compounds, such as methyl chloride and methyl bromide, are less responsive and therefore from 2 to 5 moles, in particular from 2.5 to 3.5 moles, suitably about 3 moles of the methyl compounds may be deemed to provide 1 mole of the active species. This number may be determined and verified by routine experimentation, and—without wishing to be bound by theory—it is believed that this number is higher as the methyl compound in question has a lesser ability to split off the halogen atom in question. Thus, for example, when the feed comprises $2 \times 10^{-4}$ mole-% of ethyl chloride, $3 \times 10^{-4}$ mole-% of vinyl chloride, $1 \times 10^{-4}$ mole-% of ethylene dichloride and $1.5 \times 10^{-4}$ mole-% of methyl chloride, the effective molar quantity of active halogen species may be calculated to amount to $(2 \times 10^{-4} \times 1) + (3 \times 10^{-4} \times 1) + (1 \times 10^{-4} \times 2) + (1.5 \times 10^{-4} \times \frac{1}{3}) = 7.5 \times 10^{-4}$ mole-%.

Summarizing, the effective molar quantity of active halogen species present in the feed may be calculated by multiplying the molar quantity of each of the organic halides present in the feed with a factor, and adding up the multiplication products, wherein each factor represents the number of active halogen atoms present per molecule of the organic halide in question, on the understanding that the factor for an organic halide which is a methyl compound may be in the range of from $\frac{1}{5}$ to $\frac{1}{2}$, more typically from $\frac{1}{3.5}$ to $\frac{1}{2.5}$, suitably about $\frac{1}{3}$.

The hydrocarbons present in the feed comprise the olefin and any saturated hydrocarbon present. As indicated hereinbefore, it is thought that the hydrocarbons present in the feed have the ability to remove/strip halide from the catalyst surface and the extent to which they have this ability may differ for the various hydrocarbons. In order to account for these differences (relative to ethylene), the molar quantity of each of the hydrocarbons present is multiplied with a factor, before the molar quantities are added up to calculate the effective molar quantity of the hydrocarbons. Herein, the factor of ethylene is 1, by definition; the factor for methane may be at most 0.5, or at most 0.4, typically in the range of from 0 to 0.2, more typically in the range of from 0 to 0.1; the factor for ethane may be in the range of from 50 to 150, more typically from 70 to 120; and the factor for higher hydrocarbons (i.e. having at least 3 carbon atoms) may be in the range of from 10 to 10000, more typically from 50 to 2000. Such factors may be determined and verified by routine experimentation, and—without wishing to be bound by theory—it is believed that the factor is higher as the hydrocarbon in question has a greater ability to form radicals. Suitable factors for methane, ethane, propane and cyclopropane, relative to ethylene, are about 0.1, about 85, about 1000 and about 60, respectively. As an example, when the feed comprises 30 mole-% ethylene, 40 mole-% of methane, 0.4 mole-% of ethane and 0.0001 mole-% of propane, the effective molar quantity of the hydrocarbons may be calculated to amount to $(30 \times 1) + (40 \times 0.1) + (0.4 \times 85) + (0.0001 \times 1000) = 68.1$ mole-%.

It is noted that when ethylene oxide is produced from ethylene without further hydrocarbons being present, the effective molar quantity of the hydrocarbons equals the actual molar quantity, and that the addition of ethane or higher hydrocarbons to an ethylene feed contributes significantly to the effective molar quantity, whereas there is relatively little contribution from any methane added.

Eligible values of Q are at least $1 \times 10^{-6}$, in particular at least $2 \times 10^{-6}$, and more in particular at least $3 \times 10^{-6}$. Eligible values of Q are typically most $100 \times 10^{-6}$, and more typically at most $60 \times 10^{-6}$, and in particular at most $50 \times 10^{-6}$.

The epoxidation process may be carried out using reaction temperatures selected from a wide range. Preferably the reaction temperature is in the range of from 150 to 340° C., more preferably in the range of from 180 to 325° C.

In order to reduce the effects of deactivation of the catalyst, the reaction temperature may be increased gradually or in a plurality of steps, for example in steps of from 0.1 to 20° C., in particular 0.2 to 10° C., more in particular 0.5 to 5° C. The total increase in the reaction temperature may be in the range of from 10 to 140° C., more typically from 20 to 100° C. The reaction temperature may be increased typically from a level in the range of from 150 to 300° C., more typically from 200 to 280° C., when a fresh catalyst is used, to a level in the range of from 230 to 340° C., more typically from 240 to 325° C., when the catalyst has decreased in activity due to ageing.

In accordance with the invention, the reaction temperature is increased to at least partly reduce the effect of loss of activity of the catalyst while the value of Q is maintained constant. As used herein, the value of Q is deemed to have been maintained constant if for any such temperature increase of 10° C. the value of Q has been maintained, for example, within at most 30%, typically within at most 20%, in particular at most 15%, more in particular at most 10%, most in particular at most 5%, of the value of Q at the beginning of that temperature increase.

The epoxidation process is preferably carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is as a gas phase process involving a packed catalyst bed, the GHSV is in the range of from 1500 to 10000 Nl/(l·h). Preferably, the process is carried out at a work rate in the range of from 0.5 to 10 kmole olefin oxide produced per m$^3$ of catalyst per hour, in particular 0.7 to 8 kmole olefin oxide produced per m$^3$ of catalyst per hour, for example 5 kmole olefin, oxide produced per m$^3$ of catalyst per hour. In order to reduce the effects of deactivation of the catalyst, the reaction temperature may be increased such that the work rate is substantially maintained, which means that during any 30 days' period of operation the work rate is held within a range of from 0.5 to 2, in particular 0.7 to 1.5, times the average work rate over that period. As used herein, the work rate is the amount of the olefin oxide produced per unit volume of catalyst per hour, the average work rate over a period is the total amount of the olefin oxide produced per unit volume of catalyst in that period, relative to the duration of that period and the selectivity is the molar quantity of the olefin oxide formed relative to the molar quantity of the olefin converted.

The olefin oxide produced may be recovered from the reaction mixture by using methods known in the art, for example by absorbing the olefin oxide from a reactor outlet stream in water and optionally recovering the olefin oxide from the aqueous solution by distillation. At least a portion of the aqueous solution containing the olefin oxide may be applied in a subsequent process for converting the olefin oxide into a 1,2-diol, a 1,2-diol ether or an alkanolamine.

The olefin oxide produced in the epoxidation process may be converted into a 1,2-diol, into a 1,2-diol ether or into an alkanolamine.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in presence of an acid catalyst, e.g. 0.5-1.0% w sulfuric acid, based on the total reaction mixture, at 50-70° C. at 1 bar absolute, or in a gas phase reaction at 130-240° C. and 20-40 bar absolute, preferably in the absence of a catalyst. If the proportion of water is lowered the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The conversion into the alkanolamine may comprise reacting the olefin oxide with an amine, such as ammonia, an alkyl amine or a dialkylamine. Anhydrous or aqueous ammonia may be used. Anhydrous ammonia is typically used to favour the production of monoalkanolamine. For methods applicable in the conversion of the olefin oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The alkanolamine may be used, for example, in the treating ("sweetening") of natural gas.

Unless specified otherwise, the organic-compounds mentioned herein, for example the olefins, 1,2-diols, 1,2-diol ethers, alkanolamines and organic halides, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

Having generally described the invention, a further understanding may be obtained by reference to the following examples, which are provided for purposes of illustration only and are not intended to be limiting unless otherwise specified.

EXAMPLE 1

Preparation of Catalysts

An α-alumna carrier was selected similar to "Carrier B" disclosed in U.S. Pat. No. 5,801,259, which is incorporated herein by reference. The carrier had a surface area of about 0.77 m$^2$/g, and a water absorption of about 0.39 g/g.

A silver-amine-oxalate stock solution was prepared by the following procedure:

415 g of reagent-grade sodium hydroxide were dissolved in 2340 ml de-ionized water and the temperature was adjusted to 50° C.

1699 g high purity "Spectropure" silver nitrate was dissolved in 2100 ml de-ionized water and the temperature was adjusted to 50° C.

The sodium hydroxide solution was added slowly to the silver nitrate solution, with stirring, while maintaining a solution temperature of 50° C. This mixture was stirred for 15 minutes, then the temperature was lowered to 40° C.

Water was removed from the precipitate created in the mixing step and the conductivity of the water, which contained sodium and nitrate ions, was measured. An amount of fresh deionized water equal to the amount removed was added back to the silver solution. The solution was stirred for 15 minutes at 40° C. The process was repeated until the conductivity of the water removed was less than 90 μmho/cm. 1500 ml fresh deionized water was then added.

630 g of high-purity oxalic acid dihydrate were added in approximately 100 g increments. The temperature was keep at 40° C. and the pH was kept above 7.8.

Water was removed from this mixture to leave a highly concentrated silver-containing slurry. The silver oxalate slurry was cooled to 30° C.

699 g of 92% w ethylenediamine (8% w de-ionized water) was added while maintaining a temperature no greater than 30° C. The resulting solution contained approximately 27-33% w silver.

Impregnation solutions were prepared by adding aqueous solutions comprising predetermined quantities of lithium hydroxide or nitrate, ammonium perrhenate, ammonium metatungstate, cesium hydroxide, and water to samples of a silver-amine-oxalate stock solution as described. The quantities were predetermined by calculation based on the desired composition of the catalyst to be prepared. The quantities of cesium were such that the catalysts were optimum in initial performance at the given levels of silver, rhenium, tungsten and lithium.

A carrier sample of approximately 30 g was placed under a 25 mm Hg vacuum for 1 minute at ambient temperature. Approximately 50 g of the impregnating solution was then introduced to submerse the carrier, and the vacuum was maintained at 25 mm Hg for an additional 3 minutes. The vacuum was then released and the excess impregnating solution was removed from the catalyst pre-cursor by centrifugation at 500 rpm for two minutes. The catalyst pre-cursor was then dried while being shaken at 250° C. for 5.5 minutes in a stream of air. The compositions of the obtained catalysts were as indicated in Table I.

TABLE I

| Catalyst | Silver, g/kg | Rhenium, mmole/kg | Rhenium, mmole/m² | Tungsten, mmole/kg | Cesium, mmole/kg | Lithium, mmole/kg |
|---|---|---|---|---|---|---|
| A[1]) | 132 | 0.75 | 0.0010 | 0.35 | 2.6 | 20 |
| B[1]) | 132 | 0.75 | 0.0010 | 0.35 | 3.1 | 10 |
| C[1]) | 132 | 0.75 | 0.0010 | 0.75 | 2.8 | 10 |
| D[1]) | 132 | 0.75 | 0.0010 | 0.35 | 3.1 | 20 |
| E[2]) | 147 | 0 | 0 | 0 | 2.9 | 0 |
| F[2]) | 132 | 1.5 | 0.0019 | 0.7 | 3.2 | 15 |

[1]) invention
[2]) comparative

EXAMPLE 2

Testing of Catalysts

The catalysts A, B, E and F of Example 1 were used to produce ethylene oxide from ethylene and oxygen. To do this, 1.5 to 2 g of crushed catalyst were loaded into a stainless steel U-shaped tube. The tube was immersed in a molten metal bath (heat medium) and the ends were connected to a gas flow system. The weight of catalyst used and the inlet gas flow rate were adjusted to give a gas hourly space velocity of 6800 Nl/(l·h), as calculated for uncrushed catalyst. The gas flow was 16.9 Nl/h. The inlet gas pressure was 1550 kPa.

The gas mixture passed through the catalyst bed, in a "once-through" operation, during the entire test run including the start-up, consisted of 25% v ethylene, 7% v oxygen, 5% v carbon dioxide, 63% v nitrogen and 2.0 to 6.0 parts by million by volume (ppmv) ethyl chloride.

For catalysts A, B and E, the initial reactor temperature was 180° C. and this was ramped up at a rate of 10° C. per hour to 225° C. and then adjusted so as to achieve a constant ethylene oxide content of 1.5% v in the outlet gas stream at an ethyl chloride concentration of 2.5 ppmv (Q equals $10 \times 10^{-6}$; for catalysts A, B and E, the selectivity is relatively insensitive to the ethyl chloride concentration, so that a standard 2.5 ppmv was chosen).

For catalyst F, the initial reactor temperature was 225° C. and this was ramped up at a rate of 10° C. per hour to 245° C. and then adjusted so as to achieve a constant ethylene oxide content of 1.5% v in the outlet gas stream. The ethyl chloride concentration was periodically varied from 1 to 5 ppmv to identify the level that provided the optimum selectivity. The optimum ethyl chloride concentration early in the test was 2.6 ppmv (Q equals $10.4 \times 10^{-6}$).

The initial performance data of the catalysts were obtained when the catalysts had been on stream for a total of at least 1-2 days at the constant ethylene oxide content of 1.5% v in the outlet gas stream. Then, the catalysts were subjected to accelerated ageing conditions by increasing the temperature to achieve 2.25% v ethylene oxide content in the outlet gas stream. The conditions were periodically (i.e. after every 0.08 kT/m³ cumulative ethylene oxide production) returned to 1.5% v ethylene oxide content in the outlet gas stream for 2-5 days to monitor the catalyst performance at the conditions of 1.5% v ethylene oxide content. In the run involving catalyst F, the ethyl chloride concentration was also varied periodically to identify the level that provided the optimum selectivity. Optimum selectivity was found at continually higher levels of ethyl chloride as the catalyst aged and the reaction temperature increased.

The initial (or close to initial) performance values for selectivity and reaction temperature and the values after cumulative ethylene oxide productions of 0.8 and 1.6 kT/m³ catalyst are reported in Table II, below (all values are reported at an ethylene content in the outlet gas stream of 1.5% v). A lower reaction temperature needed to accomplish a certain ethylene oxide content in the outlet gas stream is indicative for a higher activity of the catalyst. When running catalyst F, the run was discontinued at 1.5 kT/m³, because of severe deactivation of the catalyst. Just prior to the discontinuation the selectivity had dropped to 80%, the ethyl chloride concentration was 4.8 ppmv (Q equals $19.2 \times 10^{-6}$), and the reaction temperature increased to over 285° C. In addition, after a cumulative ethylene oxide production of 0.81 kT/m³, catalyst F could not be operated below the 285° C. operating limit at the conditions of 2.25% v ethylene oxide content in the outlet gas stream because of severe deactivation, so that between 0.81 and 1.5 kT/m³ the data was collected at the conditions of 1.5-2% v ethylene oxide.

TABLE II

| Catalyst | Initial selectivity, mole-% | Initial activity, ° C. | Selectivity at 0.8 kT/m³, mole-% | Activity at 0.8 kT/m³, ° C. | Selectivity at 1.6 kT/m³, mole-% | Activity at 1.6 kT/m³, ° C. |
|---|---|---|---|---|---|---|
| A[1]) | 83 | 234 | 83.5 | 255 | 81 | 269 |
| B[1]) | 84[3]) | 251[3]) | 83.5 | 257 | 81 | 270 |
| E[2]) | 82 | 233 | 80 | 246 | 79 | 247 |
| F[2]) | 90 | 253 | 87 | 264 | [4]) | [4]) |

[1]) invention
[2]) comparative
[3]) at 0.24 kT/m³
[4]) run was discontinued at a cumulative ethylene oxide production of 1.5 kT/m³, see text The Example 2 shows that at the lower content of rhenium the catalysts have an increased service life and eventually produce the olefin oxide at a higher selectivity than the catalysts which have a higher rhenium content and higher initial selectivity. The catalysts having the lower rhenium content also outperform the rhenium-free catalysts, producing more olefin oxide over their lifetime.

EXAMPLE 3

Testing of Catalysts

Catalyst B, C and D of Example 1 were tested in a similar manner, as indicated in Example 2, however, the reaction conditions were different and the testing was discontinued at a lower cumulative ethylene oxide production. The conditions were different in the following aspects: a gas hourly space velocity of 3300 Nl/(l·h), as calculated for uncrushed catalyst, the inlet gas pressure was 1550 kPa, the gas mixture passed through the catalyst bed consisted of 30% v ethylene, 8.5% v oxygen, 5% v carbon dioxide, 56.5% v nitrogen and 2.5 ppmv ethyl chloride (Q equals $8.3 \times 10^{-6}$). The ultimate ethyl chloride concentration was 2.5 ppmv. The initial performance data of the catalysts were obtained when the catalysts had been on stream for a total of at least 1-2 days at the constant ethylene oxide content of 3% v in the outlet gas stream. Then, the catalysts were subjected to accelerated ageing conditions by increasing the temperature to achieve 3.75% v ethylene oxide content in the outlet gas stream. The conditions were periodically (i.e. after every 0.08 kT/m3 cumulative ethylene oxide production) returned to 3% v ethylene oxide content in the outlet gas stream for 2 days to monitor the catalyst performance at the conditions of 3% v ethylene oxide content.

The results were as indicated in Table III.

TABLE III

| Catalyst | Initial selectivity, mole-% | Initial activity, °C. | Selectivity at 0.16 kT/m³, mole-% | Activity at 0.16 kT/m³, °C. | Selectivity at 0.24 kT/m³, mole-% | Activity at 0.24 kT/m³, °C. |
|---|---|---|---|---|---|---|
| B[1]) | 82 | 232 | 82 | 241 | 82.5 | 242 |
| C[1]) | 82 | 235 | 82 | 244 | 82 | 246 |
| D[1,2]) | 83 | 229 | 83 | 239 | 83 | 243 |

[1])invention
[2])at 0.48 kT/m³: selectivity 83 mole-%, activity 247° C.

Although the catalysts of Example 3 have different contents of tungsten, cesium and lithium, they have virtually the same performance, as a function of the cumulative ethylene oxide production.

EXAMPLE 4

Preparation and Testing of Catalysts

Catalysts were prepared in a manner as indicated in Example 1, using as a carrier an α-alumina having a surface are of 2.0 m²/g, and a water absorption of 0.42 g/g. The carrier was washed with water, according to the procedures of U.S. Pat. No. 6,368,998, which is incorporated herein by reference. The impregnation solutions were prepared by adding aqueous solutions comprising predetermined quantities of lithium hydroxide, ammonium perrhenate, cesium hydroxide, ammonium sulfate and water to the silver-amine-oxalate stock solution. The obtained catalyst comprised 145 g/kg silver, 40 mmole/kg lithium and further components as indicated in Table IV. The catalyst were tested for their initial performance using the procedures as outlined for Example 3, except that in the gas mixture the oxygen content was 8% v and the nitrogen content was 57% v. The results were as indicated in Table IV.

TABLE IV

| Catalyst | Rhenium, mmole/kg | Rhenium, mmole/m² | Sulfate, mmole/kg | Cesium, mmole/kg | Initial selectivity, mole-% | Initial acitivity, °C. |
|---|---|---|---|---|---|---|
| G[1]) | 0.5 | 0.0003 | 2 | 8.3 | 81 | 220 |
| H[1]) | 0.5 | 0.0003 | 1.5 | 7.5 | 81.5 | 218 |
| I[1]) | 0.3 | 0.0003 | 1.5 | 7.5 | 81.5 | 221 |

[1])invention

Catalyst G was tested for its initial performance at various concentrations of ethyl chloride in the gas mixture passed through the catalyst bed. The results are shown in Table V.

TABLE V

| Ethyl chloride, ppmv | Q | Initial selectivity, mole-% | Initial activity, °C. |
|---|---|---|---|
| 0 | 0 | 76.5 | 211 |
| 0.5 | $1.7 \times 10^{-6}$ | 79.5 | 211 |
| 1 | $3.3 \times 10^{-6}$ | 80.5 | 212 |
| 1.5 | $5 \times 10^{-6}$ | 81 | 213 |
| 2 | $6.7 \times 10^{-6}$ | 81 | 215 |

TABLE V-continued

| Ethyl chloride, ppmv | Q | Initial selectivity, mole-% | Initial activity, °C. |
|---|---|---|---|
| 2.5 | $8.3 \times 10^{-6}$ | 81 | 217 |
| 3.5 | $11.7 \times 10^{-6}$ | 81 | 223 |
| 5 | $16.7 \times 10^{-6}$ | 81 | 227 |

[1])for invention

Experiment 1—Testing of Catalysts

Catalysts J and K (Catalyst K for comparison) of Table VI were prepared using the method as described in Example 1. The α-alumina carriers used in the preparation of the catalysts had a surface area and a water absorption as indicated in Table VI. The catalyst had a rhenium content of 1 mmole/kg, a sulfate content of 1 mmole/kg and silver, cesium and lithium contents as indicated in Table VI.

TABLE VI

| Catalyst | Surface area, m²/g | Water absorption, g/g | Silver, g/kg | Cesium, mmole/kg | Lithium, mmole/kg | Rhenium, mmole/m² |
|---|---|---|---|---|---|---|
| J | 0.82 | 0.38 | 132 | 3.6 | 12 | 0.0012 |
| K[1]) | 0.29 | 0.29 | 110 | 2.6 | 5 | 0.0054 |

[1])for comparison

Catalysts J and K were tested for their initial performance at various concentrations of ethyl chloride in the gas mixture passed through the catalyst bed using the conditions as described in Example 3, except that the tests were operated at a constant oxygen conversion level of 40 mole-%. The results of Catalyst J and Catalyst K are shown in Tables VII and VIII, respectively.

TABLE VII (Catalyst J)

| Ethyl chloride, ppmv | Q | Initial selectivity, mole-% | Initial activity, °C. |
|---|---|---|---|
| 2 | $6.7 \times 10^{-6}$ | 83 | 231 |
| 2.5 | $8.3 \times 10^{-6}$ | 83 | 232 |
| 3.5 | $11.7 \times 10^{-6}$ | 82.5 | 232 |
| 5 | $16.7 \times 10^{-6}$ | 82.5 | 235 |

TABLE VIII (Catalyst K[1]))

| Ethyl chloride, ppmv | Q | Initial selectivity, mole-% | Initial activity, °C. |
|---|---|---|---|
| 2.5 | $8.3 \times 10^{-6}$ | 85.5 | 262 |
| 2.8 | $9.3 \times 10^{-6}$ | 86.5 | 259 |
| 3.1 | $10.3 \times 10^{-6}$ | 86 | 257 |

[1])for comparison

The results in Tables V, VII and VIII show that catalysts which have a low rhenium content as defined for use in this invention behave differently in their response to an increased organic halide content in the feed compared with catalysts having a higher rhenium content. Tables V and VII show that catalysts having the low rhenium content decrease in initial activity at an increased organic halide content. This is similar to the behavior of catalysts which are free of rhenium (see EP-A-352850, FIG. 4 therein, "CATALYST B"). Table VIII shows that catalysts having a higher rhenium content relative to the weight of the carrier increase in initial activity at an increased organic halide content, around the organic halide content level at which these catalysts show a relatively sharp selectivity optimum. This is similar to the rhenium catalysts taught in EP-A-352850 (see FIG. 4 therein, "CATALYST A"). Without wishing to be bound by theory, it is believed that this different behavior in initial performance is related to the finding of this invention that catalysts having the low rhenium content are advantageously operated in an olefin epoxidation process at a constant value of Q when the reaction temperature is increased to at least partly reduce the effect of catalyst deactivation.

We claim:

1. A process for the epoxidation of an olefin, which process comprises reacting a feed comprising an olefin, oxygen and an organic halide, in the presence of a catalyst comprising silver and rhenium deposited on a carrier, wherein the catalyst comprises rhenium in a quantity from 0.2 to 0.9 mmole/kg, relative to the weight of the catalyst, and 0.0001 to 0.0012 mmole/m$^2$, relative to the surface area of the carrier, and a tungsten copromoter in a quantity of from 0.1 to 0.75 mmole/kg, relative to the weight of the catalyst, and in which process the reaction temperature is increased to at least partly reduce the effect of loss of activity of the catalyst while the organic halide is present in a relative quantity Q which is maintained constant, which relative quantity Q is the ratio of an effective molar quantity of active halogen species present in the feed to an effective molar quantity of hydrocarbons present in the feed and wherein the selectivity of the catalyst after 1.6 kT/m$^3$ of ethylene oxide production decreases no more than about 3 mole %.

2. A process as claimed in claim 1, wherein the carrier is an α-alumina carrier having a surface area in the range of from 0.3 to 5 m$^2$/g, relative to the weight of the carrier.

3. A process as claimed in claim 2, wherein the surface area of the carrier is in the range of from 0.5 to 3 m$^2$/g, relative to the weight of the carrier.

4. A process as claimed in claim 1, wherein the silver content of the catalyst is in the range of from 50 to 400 g/kg, relative to the weight of the catalyst.

5. A process as claimed in claim 1, wherein the catalyst comprises in addition a Group IA metal or compound thereof in a quantity of from 0.01 to 500 mmole/kg, calculated as the element on the total catalyst, and a rhenium copromoter selected from molybdenum, chromium, sulfur, phosphorus, boron, and compounds thereof, in a quantity of from 0.1 to 30 mmole/kg, based on the total of the elements, relative to the weight of the catalyst.

6. A process as claimed in claim 1, wherein the olefin is ethylene and the organic halide is a chlorohydrocarbon.

7. A process as claimed in claim 1, wherein the relative quantity Q is in the range of from $2\times10^{-6}$ to $60\times10^{-6}$.

8. A process as claimed in claim 7, wherein the relative quantity Q is in the range of from $3\times10^{-6}$ to $50\times10^{-6}$.

9. A process as claimed in claim 1, wherein for any temperature increase of 10° C. to at least partly reduce the effect of loss of activity of the catalyst the relative quantity Q has been maintained within at most 20% of the value of Q at the beginning of that temperature increase.

10. A process as claimed in claim 9, wherein the relative quantity Q has been maintained within at most 15% of the value of Q at the beginning of that temperature increase.

11. A process as claimed in claim 10, wherein the relative quantity Q has been maintained within at most 10% of the value of Q at the beginning of that temperature increase.

12. A process for the production of a 1,2-diol, a 1,2-diol ether or an alkanolamine comprising converting an olefin oxide into the 1,2-diol, the 1,2-diol ether or the alkanolamine wherein the olefin oxide has been obtained by a process for the epoxidation of an olefin as claimed in claim 1.

* * * * *